United States Patent [19]

Rienstra et al.

[11] Patent Number: 5,019,502

[45] Date of Patent: May 28, 1991

[54] PROCESS FOR REMOVING BACTERIAL ENDOTOXIN FROM GRAM-NEGATIVE POLYSACCHARIDES

[75] Inventors: Mark S. Rienstra; Edgar M. Scattergood, both of Lansdale, Pa.

[73] Assignee: Merck & Company, Inc., Rahway, N.J.

[21] Appl. No.: 593,535

[22] Filed: Oct. 3, 1990

Related U.S. Application Data

[63] Continuation of Ser. No. 443,024, Nov. 30, 1989, abandoned, which is a continuation of Ser. No. 364,911, Jun. 12, 1989, abandoned.

[51] Int. Cl.$^5$ .......................... C12P 1/04; C12P 19/04; C12R 1/21
[52] U.S. Cl. ..................................... 435/101; 210/601; 210/616; 210/631; 424/88; 424/92; 435/170; 435/262; 435/280; 435/803; 435/853; 536/1.1
[58] Field of Search ............... 435/101, 170, 262, 280, 435/803; 424/88, 92; 210/601, 616, 631; 536/1.1

[56] References Cited

U.S. PATENT DOCUMENTS

| | | | |
|---|---|---|---|
| 4,220,717 | 9/1980 | Kuo | 435/101 |
| 4,474,758 | 1/1985 | Kuo et al. | 424/88 |
| 4,695,624 | 9/1987 | Marburg et al. | 424/92 |

OTHER PUBLICATIONS

Sweadner et al., App. Environl. Micro. 34:382-385 (1977).
Shands and Chun, J. Biol. Chem. 225:1221-1226 (1980).
McIntire, et al., Bio Chem. 8:4063-4066 (1969).
Ribi et al., J. Bact. 92:1493-1509 (1966).
Feldstine et al., J. Parenter. Drug Assoc. 33:125-131 (1979).
Berman et al., J. Parenter. Sci. Technol. 41:158-163 (1987).
Henderson and Beans, Kidney Internatl. 14:522-525 (1978).
Nelsen Pharm. Technol. 2:46-80 (1978).
Gerba et al., Pharm. Technol. 4:83-89 (1980).
Hou et al., App. Environ. Micro. 40:892-896 (1980).
Robinson et al., Parneteral Drug Assoc. Philadelphia, pp. 54-69 (1985).
Berger et al., Adv. Chem. Ser. 16:168-197 (1956).
Gerba et al., Appl. Environl. Micro. 50:1375-1377 (1985).
Nolan et al., Proc. Soc. Exptl. Biol. Med. 149:766-770 (1975).

*Primary Examiner*—Herbert J. Lilling
*Attorney, Agent, or Firm*—Jack L. Tribble; Joseph F. DiPrima

[57] ABSTRACT

A process for removing endotoxin from Gram-negative polysaccharides such as *H. influenzae* polyribosylribitol phosphate by mixing with a nonionic resin, a detergent and a chelating agent.

5 Claims, 2 Drawing Sheets

PROCESS FOR REMOVING BACTERIAL ENDOTOXIN FROM GRAM-NEGATIVE POLYSACCHARIDES

This is a file wrapper continuation of application Ser. No. 443,024, filed Nov. 30, 1989, which is a continuation of U.S. Ser. No. 365,911, filed June 12, 1989, both now abandoned.

BACKGROUND OF THE INVENTION

The invention is a process for removing bacterial endotoxin from gram negative polysaccharides without incurring substantial loss of polysaccharide.

Bacterial endotoxin is a potent pyrogen that can often produce fever reactions when administered to patients. Endotoxin is an integral component of the outer cell surface of Gram-negative bacteria. It exists in its natural state as a complex of lipid, carbohydrate and protein. When highly purified, endotoxin does not contain protein, and by its chemical composition is referred to as a lipopolysaccharide (see Weary and Pearson, *Bio. Pharm.* April (1988) pp. 22-29).

The outer-wall layer of Gram-negative bacteria serves as an outer barrier through which materials must penetrate if they are to reach the cell. It is selectively permeable. Generally, endotoxin is released in large amounts only when the cell wall is lysed.

Removal of contaminating endotoxin from Gram-negative polysaccharides is important when the polysaccharide is to be administered to humans. Endotoxins in large quantities can cause shock, severe diarrhea, fever and leukopenia followed by leukocytosis, and can elicit the Shwartzman and Sanarelli-Shwartzman phenomena.

U.S. Pat. No. 4,695,624 describes covalently-modified polyanionic bacterial polysaccharides, stable covalent conjugates of these polysaccharides with immunogenic proteins, and methods of preparing the polysaccharides and conjugates and of confirming covalency. The patent describes purification of the polysaccharide in Example 1, beginning in column 14. After fermentation, inactivation and cell removal, the resulting product undergoes a series of cold ethanol fractionations. Following phenol extractions are diafiltration, ethanol precipitation, ultracentrifugation in ethanol, and collection of the finished product.

Frequently, the amount of contaminating endotoxin remaining after the above-described procedure is higher than desired.

Sweadner, K. et al., *Applied and Environmental Microbiology*, Vol. 34, pp. 382-385 (1977) explains that lipopolysaccharide often exist in an aggregated state, and that dissociating the lipopolysaccharide with detergent or chelating agents can facilitate its removal from aqueous solutions by filtration. Shands, J. et al., *J. Biological Chemistry*, Vol. 255, pp. 1221-1226 (1980), show that lipopolysaccharide is associated with divalent cations, and that dispersion of Gram-negative lipopolysaccharides can be achieved using deoxycholate.

McIntire, et al, *Biochemistry*, Vol. 8, No. 10, pp. 4063-4066 (1969) describes reversible inactivation, by sodium deoxycholate, of *Escherichia coli* lipopolysaccharide. Ribi, et al., *Journal of Bacteriology*, Vol. 92, No. 5, pp. 1493-1509 (1966) described physical and biological properties of endotoxin treated with sodium deoxycholate.

Methods for removing endotoxin which are known in the art are described by Weary and Pearson (ibid): rinsing with nonpyrogenic solution (Feldstine et al., *J. Parenter. Drug Assoc.*, 33, p. 125 (1979) and Berman et al., *J. Parenter. Sci. Technol.*, 41, p. 158 (1987); distillation; ultrafiltration using membranes rated by molecular weight exclusion (Sweadner et al., *Appl. Environ. Microbiol.*, 34, p. 382 (1977) and Henderson et al., *Kidney Int.*, 14, p. 522 (1978); reverse osmosis using thin cellulose acetate or polyamide materials (Nelson, *Pharm. Technol.*, 2, p. 46 (1978); electrostatic attraction (Gerba et al., *Pharm Technol.*, 4, p. 83 (1980) and Hou et al., *Appl. Environ. Microbiol.*, 40, p. 892 (1980); hydrophobic attraction using aliphatic Polymers (Robinson et al., in *Depyrogenation* (Parenteral Drug Association, Philadelphia (1985), pp. 54-69); adsorption using activated carbon (Berger et al., *Adv. Chem. Ser.*, 16, p. 168 (1956), Gemmell et al., *Pharm J.*, 154, p. 126 (1945), and Brindle et al., *Pharm J.*, 157, p. 85 (1946); and affinity chromatography (Soter, *Bio/Technology*, 12, p. 1035 (1984).

Sawada, et al., *Applied and Environmental Microbiology*, April 1986, pp. 813-820, describe removal of endotoxin from water by microfiltration through a microporous polyethylene hollow-fiber membrane. Gerba et al., *Applied and Environmental Microbiology*, December 1985, pp. 1375-1377, describe endotoxin removal from various solution using charged nylon and cellulose-diatomaceous earth filters. Nolan et al., *Proceedings of the Society for Experimental Biology and Medicine*, Vol. 149, pp. 766-770 (1975), describe endotoxin binding by charged and uncharged resins.

It is a purpose of the present invention to provide an effective, accurate method for obtaining Gram-negative polysaccharide mixtures having low or negligable levels of endotoxin.

It is also a purpose of the present invention to remove high levels of endotoxin from Gram-negative polysaccharides without incurring substantial loss of polysaccharides.

SUMMARY OF THE INVENTION

The invention is a process for removing endotoxin from Gram-negative polysaccharides such as polyribosylribitol phosphate (PRP) using a nonionic resin, a detergent and a chelating agent. The method comprises the steps of:

(a) growing Gram-negative bacteria in fermentation broth, releasing polysaccharide into the broth and adding ethanol to remove impurities by precipitation;

(b) isolating the remaining high molecular weight species and resolubilizing them in Phenol and extracting other impurities;

(c) Precipitating and removing impurities by adding ethanol to the product of (b);

(d) drying the resulting solution of (c), and dissolving the resulting Powder in a solution of chelating agent and detergent and mixing nonionic resin under suitable conditions; and (e) removing the resin and precipitating the Polysaccharide from solution with ethanol, centrifuging the precipitate, triturating the pellet with ethanol, and drying the resulting product to form a powder.

The following abbreviations are used in the description of the present invention:

PRP—polyribosylribitol phosphate, an *H. influenzae* type b capsular polysaccharide.

LAL test value—limulus ameobocyte lysate test value, which is an indication of endotoxin level in the end-product.

LPS—lipopolysaccharide, which is the general structure of endotoxin when it is apart from the outer cell surface of Gram-negative bacteria.

EU/mcg—Endotoxin units, as measured by LAL test, per microgram PRP.

DETAILED DESCRIPTION OF THE INVENTION

Although sodium citrate is a preferred chelating agent, other chelating agents which are capable of acting on divalent calcium ions present in the solution, and which are capable of serving as a buffer for maintaining basic pH are suitable. Other suitable chelating agents include ethylenediamine-tetraacetic acids such as disodium ethylenediamine-tetraacetic acid. Preferably, the amount of chelating agent is between about 1% and about 10%, more preferably between about 2% and about 7% and even more preferably about 6%.

Although sodium deoxycholate is a preferred detergent, other detergents which are capable of breaking aggregated lipopolysaccharide are suitable. Other suitable detergents include Triton X-100, CHAPS, sodium dodecyl sulfate, and sodium lauryl sulfate. Preferably, the amount of detergent is between about 0.1% and about 2.0%, more preferably between about 0.2% and about 1.0% and even more preferably about 0.75%.

Polysaccharides from which endotoxin is removed in accordance with the present invention may be any bacterial polysaccharides with acid groups, but are not intended to be limited to any particular type. Examples of such bacterial polysaccharides include *Haemophilus influenzae* (H. flu) type b polysaccharide; *Neisseria meningitidis* (meningococcal) groups A, B, C, X, Y, W135 and 29E polysaccharides; and *Escherichia coli* K1, K12, K13, K92 and K100 polysaccharides. Particularly preferred polysaccharides, however, are those capsular polysaccharides selected from the group consisting of H. flu b polysaccharide, such as described in Rosenberg et al., *J. Biol. Chem.*, 236, pp. 2845–2849 (1961) and Zamenhof et al., *J. Biol. Chem.*, 203, pp. 695–704 (1953).

Nonionic resins to which lipopolysaccharide binds, to which polysaccharides do not bind, and which are useful in the present invention include but are not limited to Borate Avidgel (Amicon), Amberlite XAD and Amberchrome (Rohm & Haas), Octyl Cellulose (Phoenix Chem.), Silica C8 (Baker), SP and HP Series resins (e.g. SP207, HP20, HP50) (Mitsubishi Chem.). Of these resins, HP20 or HP50 is preferred because of lipopolysaccharide reduction, ease of use, availability, cost, and its propensity to avoid binding to polysaccharides. Preferably the resin is washed prior to use with pyrogen free water. More preferably, the resin is washed prior to use with acid solution, an alkali solution, or a polar solvent (e.g. ethanol or methanol) and then with pyrogen free water.

In one embodiment of the invention, a powder derived from *H. influenzae* fermentation broth containing polyribosylribitol phosphate, lipopolysaccharides, and various lipids and proteins is dissolved in a detergent/chelating agent mixture under basic pH. The resin beads are added to and mixed with the PRP solution in an orbital shaker for several hours below room temperature. The beads are then removed from solution, and the filtrate is diafiltered to remove the detergent and chelating agent. Retentate is recovered and calcium chloride added. The PRP is precipitated from solution with ethanol. The precipate is centrifuged and the pellet is triturated with ethanol and acetone. The resulting product is vacuum dried. The process using resin beads results in low levels of contaminating endotoxin without significant loss of PRP. Endotoxin reduction resulting from the process of the invention is typically 100–21,000 fold between starting and final powder PRP yield is typically at least 75% and sometimes more than 90% of the starting material.

The limulus ameobocyte lysate (LAL) test described in "Guideline on validation of the LAL test as an end-product endotoxin test for human and animal parenteral drugs, biological products, and medical devices". U.S. Department of Health and Human Services, December 1987 is used to determine endotoxin levels.

The process of the invention for removing endotoxin and preparing endotoxin-free polysaccharide is particularly advantageous when preparing polysaccharides for conjugation with proteins. Our studies have shown that conjugation efficiency is three times better with polysaccharide prepared using the process of the present invention than with polysaccharide prepared according to Marburg et al., U.S. Pat. No. 4,695,624. During preparation, the resin hydrophobically attaches to the lipid site of the lipopolysaccharide endotoxin to be removed, but does not attach in substantial quantities to other lipids that may be present. These other lipids remain in the polysaccharide solution and enhance the polysaccharide protein conjugation efficiency.

In a preferred embodiment of the invention, lipopolysaccharide is removed from a solution containing polysaccharide derived from *H. influenzae* fermentation broth by mixing it with resin, e.g. HP20 (highly porous styrene and divinylbenzene copolymer) resin, a chelating agent, e.g. sodium citrate, and a detergent, e.g sodium deoxycholate, under suitable conditions, and removing the resin by filtration. The filtrate is diafiltered, the retentate recovered, and PRP precipitated from solution with ethanol. The precipitate is centrifuged, the resulting pellet triturated with ethanol and acetone, and resulting solution vacuum dried. In the process, the detergent breaks the association of the aggregated lipopolysaccharide. The chelating agent ties up the divalent calcium ions so the vesicular structure of the lipopolysaccharide cannot be maintained, and also serves as a buffer to maintain the pH above about 8, mainly to prevent detergent gelation. The presence of both the detergent and chelating agent is essential for obtaining the superior results achievable with this process. The lipopolysaccharide is then able to bind hydrophobically to the resin. The PRP, which does not bind to the resin because it is too large to enter the pores and is hydrophilic, remains free in solution and can be recovered in the filtrate. The membrane diafiltrations which follow remove the detergent and chelating agent from the solution, and the PRP is then precipitated and dried.

The resin is mixed with a chelating agent such as sodium citrate, and a detergent such as deoxycholate. The detergent breaks the aggregated lipopolysaccharide. The chelating agent acts on divalent calcium ions present in the solution and serves as a buffer for maintaining basic pH.

The following examples illustrate the endotoxin removal procedure of the present invention as part of a Gram-negative polysaccharide preparation.

EXAMPLE 1

Preparation of *H. Influenzae* Type b Capsular Polysaccharide (PRP)

Figure 1:
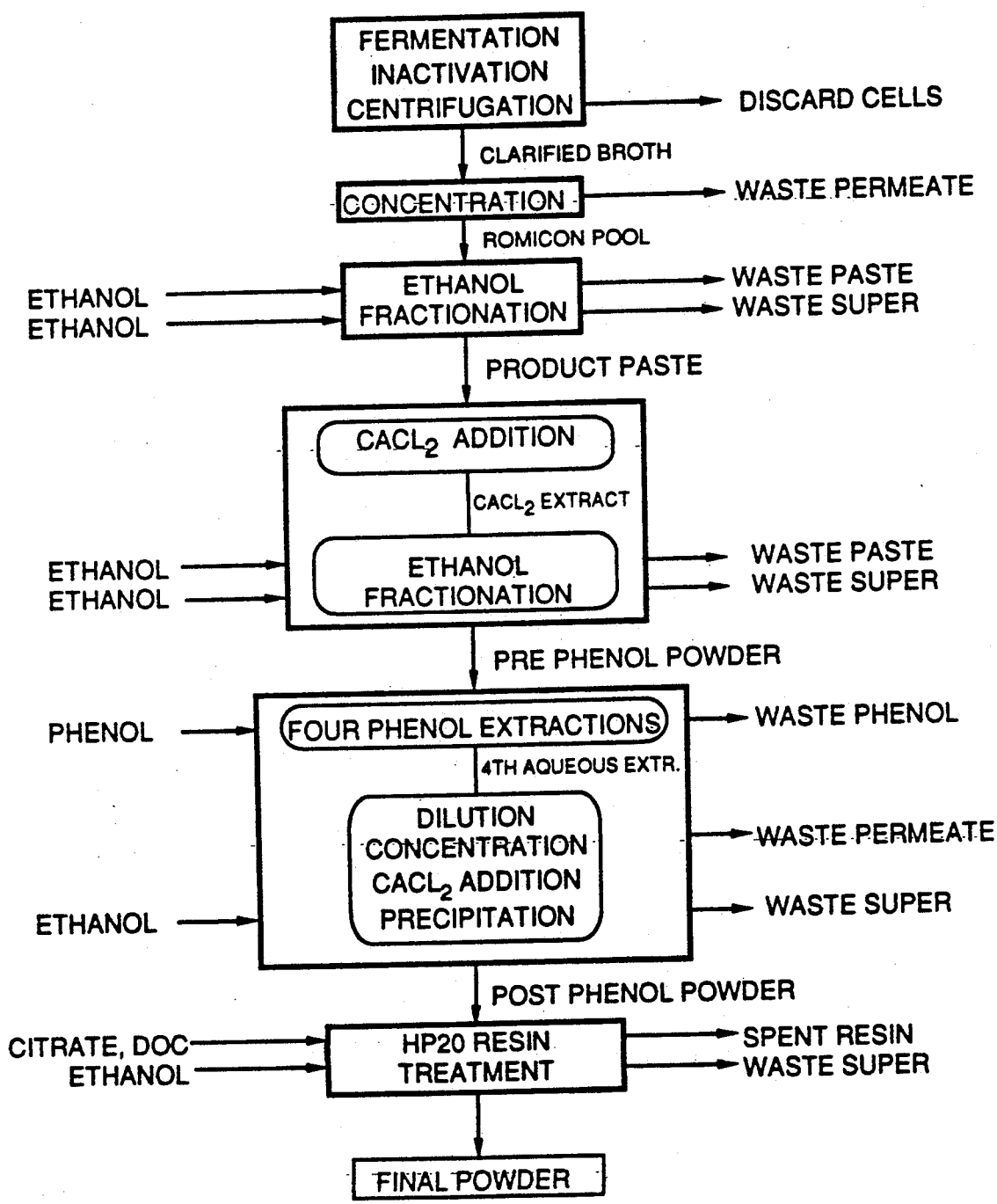
FIG. 1. Preparation of *H. influenzae* type b capsular polysaccharide.

A schematic representation of the process is shown in FIG. 1:

Fermentation

Stage A: Inoculum and Seed Development

A lyophilized tube of *Haemophilus influenzae* type b, (cultured from Ross 768, received from State University of New York) was suspended in 1 ml of sterile Haemophilus inoculum medium (see below) and this suspension was spread on nineteen Chocolate Agar Plates (BBL). After 20 hours incubation at 37° C. in a candle jar, the growth on each plate was resuspended in 1-2 ml Haemophilus inoculum medium and pooled.

| Haemophilus Inoculum Medium* | |
|---|---|
| Soy Peptone | 10 gm/liter |
| NaCl | 5 gm/liter |
| NaH$_2$PO$_4$ | 3.1 gm/liter |
| Na$_2$HPO$_4$ | 13.7 gm/liter |
| K$_2$HPO$_4$ | 2.5 gm/liter |
| Distilled Water | To Volume |

*The pH of the solution is adjusted to a target value of 7.2 ± 0.1 (a typical value was pH 7.23) and the solution was sterilized by autoclaving at 121° C. for 25 minutes.

B Stage: 2-Liter Non-baffled Erlenmeyer Flasks

One-third portions of the resuspended bacteria from "A Stage" (above) were used to inoculate three two-liter flasks, each containing about 1.0 liter of complete Haemophilus seed and production medium (see below). The flasks were then incubated at 37° C. on a rotary shaker of 200 rpm for about 5 hours. A typical OD$_{660}$ value at the end of the incubation period was 0.37.

| Complete Haemophilus Seed & Production Medium | |
|---|---|
| NaH$_2$PO$_4$ | 3.1 g/l |
| Na$_2$HPO$_4$ | 13.7 g/l |
| Soy Peptone | 10.0 g/l |
| Yeast extract diafiltrate (1) | 10.0 ml/l |
| K$_2$HPO$_4$ | 2.5 g/l |
| NaCl | 5.0 g/l |
| Glucose (2) | 5.0 g/l |
| Nicotinamide adenine dinucleotide (NAD) (3) | 2.0 mg/l |
| Hemin (4) | 5.0 mg/l |

The salts and soy peptone were dissolved in small volumes of hot, pyrogen-free water and brought to correct final volume with additional hot, pyrogen-free water. The fermenters or flasks were then sterilized for about 25 minutes at 121° C. and after cooling, yeast extract diafiltrate (1), glucose (2), NAD (3), and hemin (4) were added aseptically to the flasks or fermenters prior to inoculation.

(1) Yeast extract diafiltrate: 100 g brewers' yeast extract (Amber) was dissolved in 1 liter distilled water and ultrafiltered in an Amicon DC-30 hollow fiber with H10X50 cartridges to remove molecules with m.w. 50,000. The filtrate was collected and passed through a 0.22μ membrane as a sterile product.

(2) Glucose was prepared as a sterile 25% solution in glass-distilled water.

(3) A stock solution of NAD containing 20 mg/ml was sterilized by filtration through a Millipore filter (0.22μ) and added aseptically just prior to inoculation.

(4) A stock solution of Hemin 3X was prepared by dissolving 200 mg in 10 ml of 0.1M NaOH and the volume adjusted with distilled, sterilized water to 100 ml. The solution was sterilized for 20 minutes at 121° C. and added aseptically to the final medium prior to inoculation.

C Stage: 70-Liter Seed Fermenter

Three liters of the product of "B Stage" was used to inoculate a 70-liter fermenter containing 41.4 liters of complete haemophilus seed and production medium (prepared as described above) and 17 ml UCON B625 antifoam. The pH started at 7.4.

The fermentation was maintained at 37° C. with 100 rpm agitation and monitored by optical density (O.D.) and pH determination until a typical O.D. of 0.39 was reached (after about 5.5 hours).

D Stage: 800-Liter Production Fermenter

Approximately 40 liters of the product of "C Stage" was used to inoculate an 800-liter fermenter containing 570 liters of production medium (prepared as described above), scaled to the necessary volume and 72 ml of UCON LB625 antifoam.

The fermentation was maintained at 37° C. with 100 rpm of agitation, with the O.D. and pH levels being checked about every two hours until the O.D. was similar for a two-hour period, at which time the fermentation was terminated (a typical final O.D. was 0.54 after 12 hours).

Harvest and Inactivation

Approximately 600 liters of the batch was inactivated by harvesting into a "kill tank" containing 12 liters of 1% thimerosal.

Clarification

After 8 hours inactivation at 4° C., the batch was centrifuged in 4-in. bowl Sharples centrifuges at a flow rate adjusted to maintain product clarity (variable between 1.3 and 3.0. liters/min). The supernatant obtained after centrifugation (15,000 rpm) was used for product recovery.

Isolation and Concentration by Ultrafiltration

The supernatant fluid from two production fermentations was pooled and concentrated at 2°-8° C. in a Romicon ultrafiltration unit with ten (50,000 Daltons cut-off) hollow fiber cartridges (275 ft$^2$ membrane area) such that after approximately 4.5 hours, 1200 liters had been concentrated to 32.5 liters. The filtrate was discarded.

48% and 61% Ethanol Precipitation

To the 32.5 liters of Romicon retentate, 30 liters of 95% ethanol was added dropwise over 1 hour with stirring at 4° C. to a final concentration of 48% ethanol by volume. The mixture was stirred two additional hours at 4° C. to ensure complete precipitation, and the supernatant fluid was collected through a single 4-inch Sharples centrifuge at 15,000 rpm (flow rate=0.27 liters/min). The insoluble pellet was discarded and the clarified fluid was brought to 61% ethanol with the addition of 20.8 liters of 95% ethanol over a one hour period. The mixture was stirred for three additional hours to insure complete precipitation.

Recovery of the Second Pellet

The resulting 48% ethanol soluble-61% ethanol insoluble precipitate was collected by centrifugation in the 4-inch Sharples centrifuge at 15,000 rpm (flow rate=0.62 liters/min.) and the 61% ethanol supernatant fluid was discarded. The crude product yield was 0.377 kg of wet paste.

Calcium Chloride Extraction

The 377 grams of 61% ethanol insoluble material, was mixed in a Daymax dispersion vessel at 2°-8° C. with 6.5 liters of cold, glass-distilled water. To this mixture, 6.5 liters of cold 2M $CaCl_2 \cdot H_2O$ was added, and the mixture (final concentration=1.0M $CaCl_2$) was extracted at 4° C. for 15 minutes. The vessel was then rinsed out with 2 liters of 1M $CaCl_2 \cdot H_2O$ resulting in 15 liters final volume.

23% Ethanol Precipitation

The 15 liters of $CaCl_2$ extract from above was brought to 23% ethanol by adding 4.48 liters of 95% ethanol dropwise, with stirring, at 4° C. over 30 minutes. After additional stirring for 17 hours, the mixture was centrifuged through a K2 Ultracentrifuge at 25,000 rpm (flow rate-165 ml/min) for 6.5 hours at 4° C. The supernatant fluid was decanted through cheese cloth to remove lipid-like floating material and the insoluble pellet was discarded.

37% Ethanol Precipitation and Collection of Crude Product Paste

The 23% ethanol-soluble supernatant fluid was brought to 37% ethanol by the addition of 4.33 liters of 95% ethanol, dropwise with stirring, over a 30 minute period. The mixture was then allowed to stand with agitation for one hour, then without agitation for 14 hours, to ensure complete Precipitation. The resulting mixture was then centrifuged in a 4-inch Sharples unit at 15,000 rpm (flow rate=0.2 liters/min) to collect the pelleted crude polysaccharide (referred to hereinafter as pre-phenol powder).

Trituration

The pellet from the centrifugation was transferred to a 1-gallon Waring Blender containing 1 liter of absolute alcohol and blended for 30 seconds at the highest speed. Blending was continued at 30 seconds on and 30 seconds off until a hard, white powder resulted. The powder was collected on a Buchner funnel with a teflon filter disc and washed sequentially in situ with two 1-liter portions of absolute ethanol and two 2-liter portions of acetone. The material was then dried in vacuo, at 4° C., for 24 hours, resulting in 68 g (dry weight) of product.

Phenol Extraction

The 68 grams of dry material from the trituration step was resuspended in 12 liters of 0.488M sodium acetate, pH 6.9, with the aid of a Daymax dispersion vessel. The sodium acetate solution was immediately extracted with 4.48 liters of a fresh aqueous phenol solution made as follows: 900 ml of 0.488M sodium acetate, pH 6.9, was added to a five-pound bottle of phenol (Mallinckrodt crystalline) in a 20-liter pressure vessel and mixed until a complete solution was effected. Each phenol extract was centrifuged for 2½ hours at 30,000 rpm and 4° C. in the K2 Ultracentrifuge (Electronucleonics) in order to break the emulsion. The aqueous effluent was extracted three additional times with 3.2 fresh aqueous phenol solution in a similar manner. The phenol phases were discarded.

Diafiltration

The aqueous phase from the phenol extractions above (17.6 liters) was diluted with 300 liters of cold, glass-distilled water and diafiltered at 4° C. on an Amicon DC-30 ultrafiltration apparatus using 3 H10P10 cartridges. The Amicon unit was rinsed and the rinse added to the retentate, such that the final volume was 17.5 liters. The ultrafiltrate was discarded.

67% Ethanol Precipitation 0.438 liters of 2.0M $CaCl_2$ was added to the 17.5 liters of dialysate from the previous step (final $CaCl_2$ concentration was 0.05M) and the solution was made 67% ethanol with dropwise addition over one hour of 35.88 liters of 95% ethanol to the rapidly-stirring solution. After 4 hours of agitation, then standing for 12 hours more at 4° C., the clear supernatant fluid was siphoned off and the precipitate was collected by centrifugation in the 4-inch Sharples centrifuge (15,000 rpm), at 4° C. for 45 minutes. The resulting polysaccharide pellet was triturated in a 1-gallon Waring blender using the 30 seconds on 30 seconds off method with 2 liters of absolute ethanol, collected on a Buchner funnel fitted with a teflon filter disc, and washed in situ with four 1-liter portions of absolute ethanol followed by two 1-liter portions of acetone. The sample was then dried in a tared dish in vacuo at 4° C. for 20 hours. The yield was 39 grams of dry powder (referred to hereinafter as post-phenol powder).

Endotoxin Removal

Figure 2:
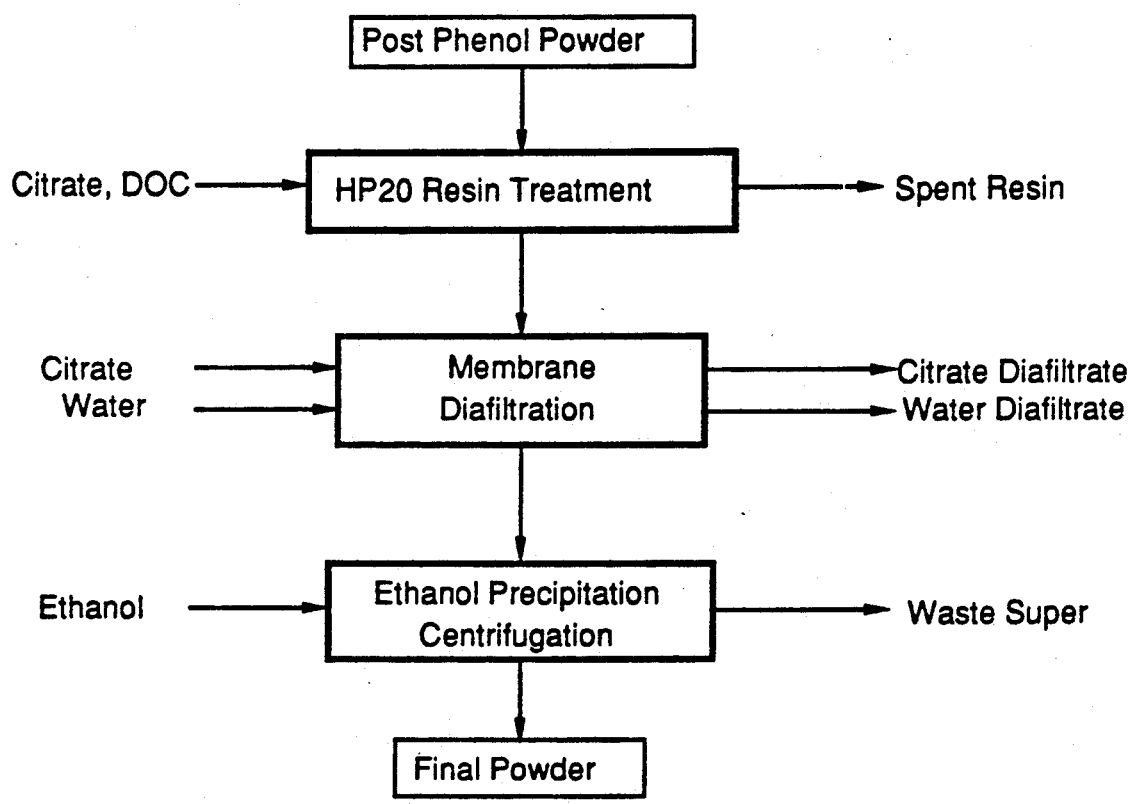
FIG. 2. Endotoxin removal using resin and ethanol precipitation.

A schematic of the procedure is shown FIG. 2.

PRP post-phenol powder was dissolved, at 2 mg/ml, in a solution of 3% sodium citrate and 0.5% sodium deoxycholate at pH 8-9. HP20 resin was added at 30 grams resin per gram PRP (the resin was washed prior to use with the pyrogen free water). The loose beads were mixed with the PRP solution on an orbital shaker for 3 hours at 4° C. After mixing, the beads are removed from the solution in a stainless steel filter funnel. Filtrate is then diafiltered in an Amicon H1P30-20 hollow fiber cartridge (0.06 m² surface area) vs. 5 vol. of 1.5% citrate followed by 10 vol. of pyrogen free water, maintaining an estimated PRP concentration of $\leq 2.5$ mg/ml to remove detergent and chelating agent. The retentate is recovered and 2M calcium chloride is added to achieve a final calcium chloride concentration of 0.05M. PRP is precipitated from solution with excess 95% ethanol. The precipitate is centrifuged at 13,000×g for 30 minutes, the pellet triturated with absolute ethanol and acetone, and then vacuum dried. The final powder is transferred to a sample container and frozen at −70° C.

Endotoxin level was reduced between 100 and 21,000 fold between starting and final powders. PRP yield is between 75 and >90% from starting to final powder.

900 mg of post-phenol powder was processed. Quantitative determination of endotoxin was done using the well-known limulus ameobocyte lysate (LAL) test.

LAL was reduced after the various process steps as shown below (1 EU/mcg of polysaccharide = 100 ppm):

LAL test value (ppm)

initial—18,000
after HP20 resin treatment—12
after Hollow Fiber treatment—12
final powder—6

PRP loss caused by the process was not substantial. Amounts of PRP remaining at various stages of the process, represented by percentage of the initial amount, are shown below:

initial—100%
after HP20 resin treatment—93
after Hollow Fiber treatment—90
final powder—75

EXAMPLES 2, 3, 4, 5, 6 and 7

Following the procedure for endotoxin removal described in Example 1, maintaining a concentration of sodium deoxycholate of 0.5%, and beginning with powder having LPS of 260 EU/mcg, we obtained the following reduction in LAL with these varying amounts of sodium citrate:

|  | % Sodium Citrate | LPS EU/mcg |
|---|---|---|
| Example 2 | 2 | 22 |
| Example 3 | 3 | 4.2 |
| Example 4 | 4 | 1.0 |
| Example 5 | 5 | 0.6 |
| Example 6 | 6 | 0.9 |
| Example 7 | 7 | 0.6 |

EXAMPLES 8, 9 AND 10

Following the procedure for endotoxin removal described in Example 1, maintaining a concentration of sodium citrate of 6%, and beginning with powder having LPS of 260 EU/mcg, we obtained the following reduction in LAL with these varying amounts of deoxycholate:

|  | % Sodium Deoxycholate | LPS EU/mcg |
|---|---|---|
| Example 8 | 0.25 | 15 |
| Example 6 | 0.5 | 0.9 |
| Example 9 | 0.75 | 0.01 |
| Example 10 | 1.0 | 0.4 |

EXAMPLES 11, 12, 13, 14 AND 15

Following the general procedure in Example 1, these examples include description of process variations and the resulting LPS obtained from powder originally having 260 EU/mcg.

| Process Variation |  | LPS Avg. EU/mcg |
|---|---|---|
| Example 11 | After treatment in accordance with Example 3, the procedure is repeated. | 0.4 |
| Example 12 | After treatment according to Example 3, filtrate is diafiltered with 3% sodium citrate, sodium deoxycholate is added, and the solution treated for three additional hours with the original HP-20 resin. |  |
| Example 13 | After three hours of HP-20 treatment according to Example 3, an equal volume of 3% citrate with 0.5% sodium deoxycholate was added to the mixture and resin treatment continued for another three hours. | 0.4 |
| Example 14 | After three hours according to Example 3, sodium citrate and sodium deoxycholate powder were added and the resin treatment continued for another three hours. | 0.2 |
| Example 15 a, b | (a) Six percent sodium citrate with 0.5% sodium deoxycholate or (b) 6% sodium citrate with 1% sodium deoxycholate was used for three hours. | (a) 0.3 (b) 0.1 |

EXAMPLE 16

All of the process steps of Example 1 are used, except that the resin is packed in a column, rather than mixed in batch with PRP. Thus, the PRP is dissolved in a solution of sodium citrate and sodium deoxycholate, and the resulting solution is passed through the column. The resulting product is similar to that obtained om Example 1.

All of the process steps of Example 1 are repeated, except that the resin is packed in a cartridge, rather than mixed in batch with PRP. Thus, the PRP is dissolved in a solution of sodium citrate and sodium deoxycholate, and the resulting solution is circulated through the cartridge. The resulting product is similar to that obtained in Example 1.

EXAMPLE 18

In this example, all of the process steps of Example 1 are followed. In accordance with this procedure, 1 gram of PRP is processed. Results are set forth below:

LAL test value (ppm)

initial—11,000
after HP20 resin treatment—15
after Hollow Fiber treatment—11.2
final powder—6

PRP loss caused by the process was not substantial. Amounts of PRP remaining at various stages of the Process, represented by percentage of the initial amount, are shown below:

initial—100%
after HP20 resin treatment—96
after Hollow Fiber treatment—93
final powder—91

The material obtained by this process conformed to all current chemical specifications.

EXAMPLE 19

In this example, the method of Example 1 is followed except that 6% sodium citrate and 0.75% sodium deoxycholate are used instead of 3% sodium citrate and 0.5% sodium deoxycholate. The method was applied to four different lots of post-phenol powder material, (a, b, c and d). LAL test value (EU/mcg) reductions achieved are shown below:

| | LAL test value (EU/mcg) | |
|---|---|---|
| | Initial | Final |
| a. | 22 | 0.0012 |
| b. | 126 | 0.006 |
| c. | 190 | 0.009 |
| d. | 270 | 0.012 |

The polysaccharide product resulting from the endotoxin removal procedure of the invention is especially useful where endotoxin-free Gram-negative polysaccharide is desirable. It readily conjugates to proteins, e.g. immunogenic proteins, such as in the manner described in Marburg et al. (ibid). The conjugates are stable polysaccharide-protein conjugates, coupled through bigeneric spacers containing a thioether group and primary amine, which form hydrolytically-labile covalent bonds with the polysaccharide and the protein. Exemplary conjugates are those which may be represented by the formulae Ps-A-E-S-B-Pro or Ps-A'-S-E'-B'-Pro, where Ps represents a polysaccharide, Pro represents a bacterial protein, and A-E-S-B and A'-S-E'-B' constitute bigeneric spacers which contain hydrolytically-stable covalent thioether bonds, and which form covalent bonds (such as hydrolytically-labile ester or or amide bonds) with the macromolecules, Pro and Ps. The specific definitions of S,E,S,B,A',E' and B' are presented in Marburg et al., the contents of which are hereby incorporated by reference. Procedures for preparing polysaccharides and proteins for conjugation, performing conjugation, and determining conjugation, are all described in the patent.

What is claimed is:

1. A method for removing endotoxins from a Gram-negative bacteria fermentation product which comprises the steps of:
   (a) growing Gram-negative bacteria in fermentation broth, releasing polysaccharide into the broth, and adding alcohol to remove impurities by precipitation;
   (b) isolating the high molecular weight species and resolubilizing them in phenol and extracting other impurities;
   (c) precipitating and removing impurities by adding ethanol to the product of (b);
   (d) drying the resulting solution of (c), and dissolving the resulting powder in a solution of chelating agent and detergent and mixing nonionic resin under suitable conditions; and
   (e) removing the resin, chelating agent and detergent and precipitating the polysaccharide from solution with ethanol, centrifuging the precipitate, triturating the pellet with ethanol, and drying the resulting product to form a powder.

2. The method of claim 1 wherein the polysaccharide is polyribosylribitol phosphate.

3. The method of claim 1 wherein the chelating agent is sodium citrate.

4. The method of claim 1 wherein the detergent is sodium deoxycholate.

5. The method of claim 1 wherein the resin is a highly porous styrene and divinylbenzene copolymer.